(12) United States Patent
Hettrick et al.

(10) Patent No.: US 9,375,578 B2
(45) Date of Patent: Jun. 28, 2016

(54) CARDIAC PACING METHODS AND APPARATUS

(75) Inventors: Douglas A. Hettrick, Andover, MN (US); Todd Jon Sheldon, North Oaks, MN (US); Paul D. Ziegler, Minneapolis, MN (US); David E. Euler, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 2470 days.

(21) Appl. No.: 12/178,534

(22) Filed: Jul. 23, 2008

(65) Prior Publication Data

US 2010/0023079 A1    Jan. 28, 2010

(51) Int. Cl.
   *A61N 1/368* (2006.01)

(52) U.S. Cl.
   CPC .............. *A61N 1/368* (2013.01); *A61N 1/3682* (2013.01)

(58) Field of Classification Search
   CPC .......................... A61N 1/368; A61N 1/3682
   USPC .................................. 607/9, 17, 27
   See application file for complete search history.

(56) References Cited

U.S. PATENT DOCUMENTS

| | | | |
|---|---|---|---|
| 4,998,974 A | 3/1991 | Aker | |
| 5,024,222 A | 6/1991 | Thacker | |
| 5,179,949 A * | 1/1993 | Chirife | 607/9 |
| 5,334,222 A | 8/1994 | Salo et al. | |
| 5,861,007 A | 1/1999 | Hess et al. | |
| 6,859,665 B2 | 2/2005 | Ding et al. | |
| 6,937,902 B2 | 8/2005 | Lidman et al. | |
| 7,130,683 B2 | 10/2006 | Casavant et al. | |
| 2002/0049478 A1 | 4/2002 | Ding et al. | |
| 2003/0074026 A1 | 4/2003 | Thompson et al. | |
| 2006/0041279 A1 * | 2/2006 | Yu et al. | 607/9 |
| 2006/0167509 A1 * | 7/2006 | Boute et al. | 607/9 |
| 2006/0241703 A1 | 10/2006 | Ding et al. | |

FOREIGN PATENT DOCUMENTS

WO    WO 2007/090003 A1    8/2007

OTHER PUBLICATIONS

P0025507.01 (PCT/US2009/050798) PCT Notification of Transmittal of the International Search Report and the Written Opinion of the International Searching Authority.

* cited by examiner

*Primary Examiner* — Tammie K Heller
(74) *Attorney, Agent, or Firm* — Evans M. Mburu

(57) ABSTRACT

A method and apparatus is provided for determining whether a current atrial-ventricular (AV) delay during cardiac pacing is appropriate for proper mechanical coupling of the atrium and ventricle. If proper mechanical coupling is determined to not exist, an additional atrial contraction is induced within the same ventricular cycle to maintain atrial-ventricular mechanical coupling.

10 Claims, 4 Drawing Sheets

CARDIAC PACING METHODS AND APPARATUS

TECHNICAL FIELD

This disclosure relates generally to medical devices and more particularly to a system and method for compensating for long atrial-ventricular (AV) delays encountered in cardiac pacing.

BACKGROUND

Various pacing methods such as "Search AV" and "Managed Ventricular Pacing®" are designed to promote intrinsic conduction of paced or intrinsic atrial events to the ventricle. Such methods are illustrated, for example, in U.S. Pat. Nos. 7,130,683 and 5,861,007, respectively entitled "Preferred ADI/R: A Permanent Pacing Mode to Eliminate Ventricular Pacing While Maintaining Back Support" and "Adaptive Search AV and Auto PVARP Adaptation to Same with Additional Benefit," both of which are incorporated by reference in their entireties herein.

Clinically, such pacing methods may result in very long atrial-ventricular (AV) delays (e.g., longer than 300 ms). Such long AV delays may result in short ventricular—atrial (VA) intervals, depending on, for example, the heart rate, atrial pressure, duration of ventricular systole, and the rate and extent of ventricular relaxation. In some of these instances, the result may be atrial contraction against a closed mitral (or tricuspid) valve that results in increased atrial pressure and deceleration or frank reversal of pulmonary venous (or caval) flow. Thus, atrial function, ventricular filling (diastolic ventricular function), and ventricular systolic performance may be compromised under these circumstances.

SUMMARY

In one or more embodiments, a method and apparatus are provided for determining whether the current AV delay in a patient is appropriate for proper mechanical coupling of the atrium and ventricle. If not, an additional atrial contraction is induced within the same ventricular cycle to maintain atrial-ventricular mechanical coupling.

In one or more embodiments, the method determines if the duration of the current AV interval is too long and if the next ventricular-atrial (VA) interval is too short to allow for adequate ventricular-atrial mechanical coupling. Thus, if a long AV interval is detected along with a short VA interval, an additional atrial pace is provided.

In one or more embodiments, the ratio of the AV to VV interval is determined in the absence of ventricular paced events, where "VV" is the interval between ventricular activations. For example, if the ratio of AV:VV exceeds >0.5 (or some other user selectable value), an additional atrial pace is provided after a certain programmable duration has elapsed following the first paced or intrinsic atrial event in the cycle. After provisioning of the additional atrial pace, one or more safety checks may be performed to determine if the additional pace was safely tolerated by the patient. In one illustrative embodiment, the method is automatically disabled if the additional atrial pace conducted 1:1, further increased AV conduction block (Wenkebach), induced premature atrial contractions (PACs), or initiated atrial tachycardia or atrial fibrillation.

DRAWINGS

The above-mentioned features of the present disclosure will become more apparent with reference to the following description taken in conjunction with the accompanying drawings wherein like reference numerals denote like elements and in which.

DETAILED DESCRIPTION

This disclosure provides a method and apparatus for detecting and responding correctively to inordinately long atrial-ventricular (AV) delays. In one or more embodiments, the method and apparatus may be implemented in implantable medical devices (IMDS) that include sensing capabilities for monitoring physiological conditions and which may also include alert and therapy delivery capabilities. An IMD in which the method and apparatus are implemented may be primarily intended for detecting and/or responding to heart-related conditions or may primarily be intended for other purposes. For example, the IMD may comprise any type of implanted device including, but not limited to cardiac pacemakers, implantable cardioverter-defibrillators (ICDs), implantable combination pacemaker-cardioverter-defibrillator (PCDs), and so on.

A wide variety of IMDs have been developed in order to monitor patient conditions and deliver therapy to the patient. An IMD typically includes a hermetically sealed housing coupled to one or more leads that are surgically implanted inside a patient for sensing conditions or for administering therapy. The IMD may provide therapeutic stimulation to the patient or may deliver drugs or agents to the patient. Alternatively or additionally, the IMD may have sensing or monitoring capabilities. For example, the IMD may sense information within a patient and store the sensed information for subsequent analysis. The sensed information may be used directly by the IMD to adjust or control the therapy that is delivered to the patent. Telemetry is used to communicate sensed information from the IMD to an external medical device so that analysis of the sensed information can be performed. Telemetry is further used to communicate information or instructions from external medical devices to the IMD.

Figure 1:
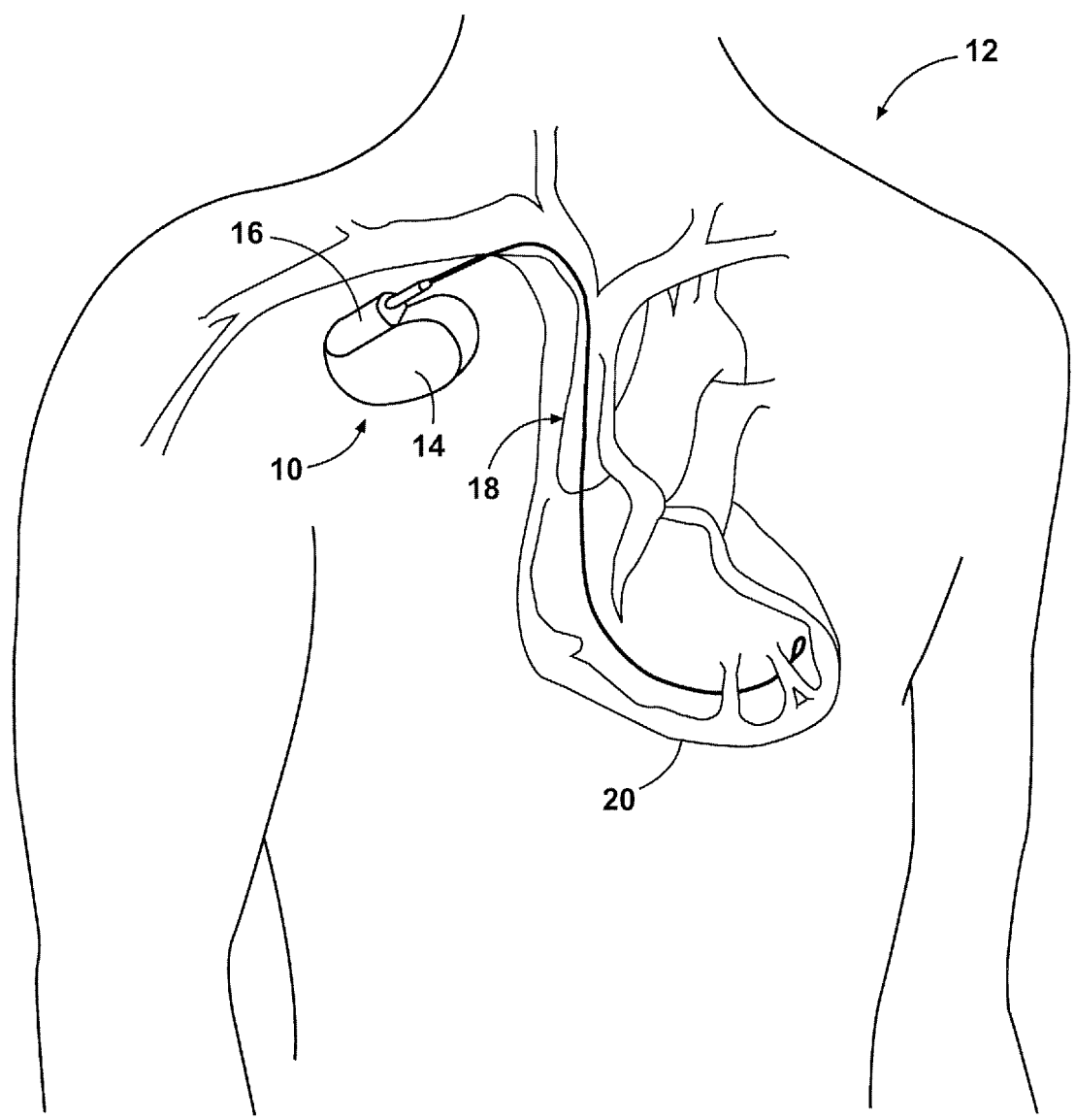
FIG. 1 illustrates an implantable medical device in accordance with an embodiment of the present disclosure implanted in a human body.

FIG. 1 is a simplified schematic view of one type of implantable medical device ("IMD") 10 implanted within a human body 12 in which one or more embodiments of the invention may be implemented. IMD 10 comprises a hermetically sealed enclosure 14 and connector module 16 for coupling IMD 10 to electrical leads and other physiological sensors arranged within body 12, such as pacing and sensing leads 18 connected to portions of a heart 20 for delivery of pacing pulses to a patient's heart 20 and sensing of heart 20 conditions. IMD 10 collects and processes data from one or more sensors for deriving parameters used in tracking various atrial and ventricular related events and implementing the illustrative embodiment hereafter described, in which IMD 10 is implanted.

Figure 2:
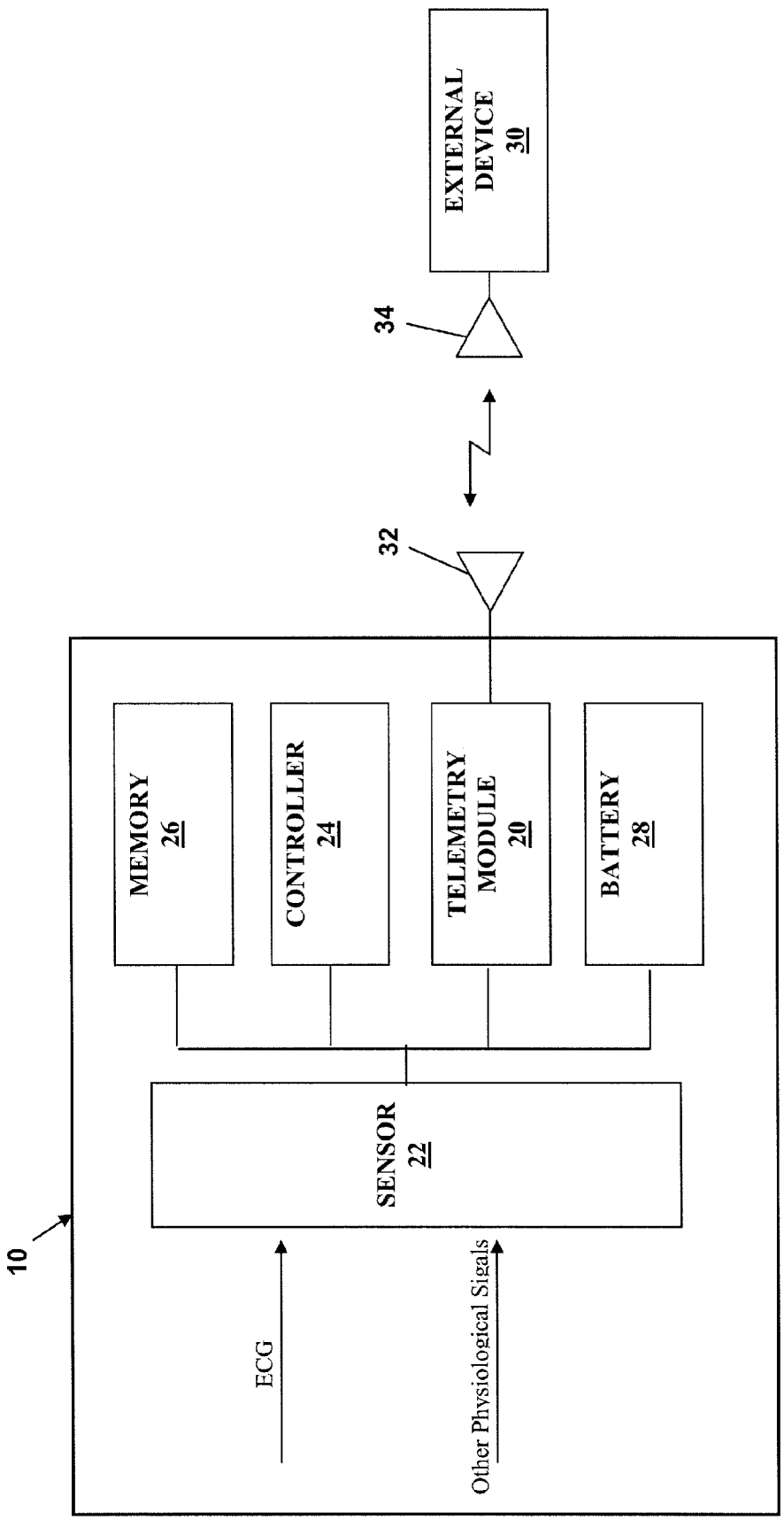
FIG. 2 is a block diagram illustrating the various components of one embodiment of an implantable medical device configured to operate in accordance with the present disclosure.

FIG. 2 is a block diagram illustrating the constituent components of IMD 10 in accordance with one or more embodiments having a microprocessor-based architecture. IMD 10 is shown as including telemetry module 20, at least one sensor 22 for sensing physiological signals, processor or controller 24, memory 26, battery 28 and other components as appropriate to produce the desired functionalities of the device.

The controller 24 may be implemented with any type of microprocessor, digital signal processor, application specific integrated circuit (ASIC), field programmable gate array (FPGA) or other integrated or discrete logic circuitry programmed or otherwise configured to provide functionality as described herein. Controller 24 executes instructions stored in memory 26 to provide functionality as described herein. Instructions provided to controller 24 may be executed in any manner, using any data structures, architecture, programming language and/or other techniques. Memory 26 is any storage medium capable of maintaining digital data and instructions provided to controller 24 such as a static or dynamic random access memory (RAM), read-only memory (ROM), non-volatile random access memory (NVRAM), electrically erasable programmable read-only memory (EEPROM), flash memory, or any other electronic, magnetic, optical or other storage medium.

As further shown in FIG. 1, IMD 10 may receive one or more cardiac leads 18 for connection to circuitry enclosed within the housing 14. In one or more embodiments, IMD 10 collects electrocardiogram (ECG) signals or other physiological signals for use in deriving one or more heart related parameters, such as AV, VA, VV, or other parameters for use in detecting the performance of the heart or other heart-related conditions, as known to those skilled in the art. Other auxiliary leads may further be connected to both IMD 10 and the patient's body for detecting other physiological conditions.

Cardiac leads 18 may include, for example, pacing electrodes and defibrillation coil electrodes (not shown). In addition, cardiac leads 18 may deliver pacing stimuli in a coordinated fashion to provide pacing pulses, cardiac resynchronization, extra systolic stimulation therapy, or other benefits.

In operation, IMD 10 obtains data from physiological signals via electrodes and/or sensors 22 deployed on leads 18 and/or other sources. This data is provided to controller 24, which suitably analyzes the data, stores appropriate data in memory 26, and/or provides a response or report as appropriate.

Communication between IMD 10 and another device can occur via telemetry, such as a long-distance telemetry system through the telemetry module 20. Telemetry module 20 may comprise any unit capable of facilitating wireless data transfer between IMD 10 and an external device 30, where external device 30 may comprise an external medical device, a programming device, a remote telemetry station, a physician-activated device, a patient-activated device, a mobile hand-held unit (e.g., mobile phone, PDA, etc.), a personal computer, an in-home monitoring device, a patient-wearable device, a display device or any other type of device capable of sending and receiving signals to and from IMD 10. Telemetry module 20 and external device 30 are respectively coupled to antennas 32 and 34 for facilitating the wireless data transfer. Telemetry module 20 may be configured to perform any type of wireless communication. For example, telemetry module 20 may send and receive radio frequency (RF) signals, infrared (IR) frequency signals, or other electromagnetic signals.

IMD 10 includes at least one sensor 22 configured to sense at least one physiological signal or condition, from which a physiological parameter can be determined. Sensors 22 can monitor electrical, mechanical, chemical, or optical information that contains physiological data of the patient.

Figure 3:
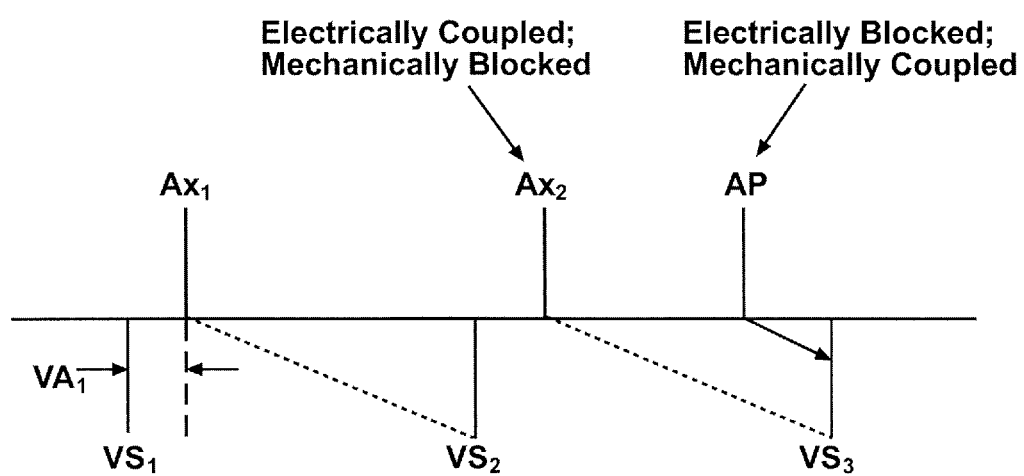
FIG. 3 is a waveform diagram useful in describing an illustrative embodiment according to the present disclosure.

FIG. 3 illustrates one condition addressed by the subject disclosure and comprises a graph of atrial events Ax (sensed or paced) and intrinsic ventricular sensed events VS. A ventricular sense is generally denoted as an R wave on a representative ECG. Two R-R intervals (intervals between sequential ventricular events (VS)) are depicted on FIG. 3, the first being the interval between ventricular beats $VS_1$ and $VS_2$ and the second being the interval between ventricular beats $VS_2$ and $VS_3$.

During the first R-R interval, the atrial beat $Ax_1$ will likely not result in effective atrial contribution, since the VA interval ($VA_1$) is too short to allow ventricular relaxation and mitral valve opening. In the second R-R interval, the same situation is present; however, now an additional atrial paced event AP is provided. In this case, the AV node is still refractory from the stimulus provided by $Ax_2$, which will eventually trigger $VS_3$. Thus, the AP is electrically blocked at the AV node from reaching the ventricles. However, the atrial contraction that results from the AP will be better "mechanically coupled" to the ventricle, since the ventricle will still be in the later phase of diastole, when atrial contraction is appropriate. Therefore, the pace AP will be electrically blocked but mechanically coupled. In this case, intrinsic ventricular activation with an appropriate atrial contraction is maintained.

Figure 4:
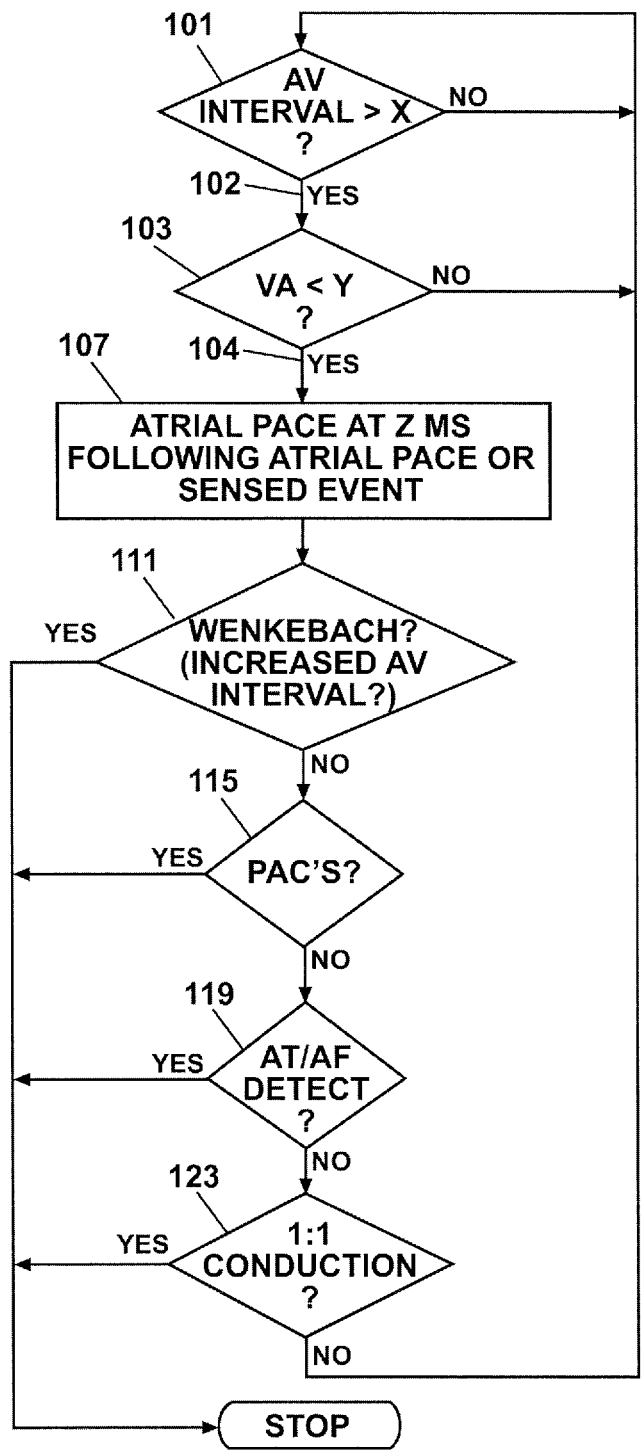
FIG. 4 is a flow diagram of an implementation of a method for detecting and responding to an undesirable AV delay according to an illustrative embodiment.

The flow diagram of FIG. 4 presents an illustrative method in accordance with one or more embodiments for determining and applying an additional atrial paced event AP in order to institute an additional atrial contraction within the same ventricular cycle, as described in connection with FIG. 3. The flow diagram of FIG. 4 in particular illustrates tests performed and actions which may be implemented, for example, by IMD 10 including sensor 22 and controller 24 (e.g. microprocessor) resident in IMD 10 of FIGS. 1 and 2.

According to FIG. 4, operation 101 is first performed to determine whether a first atrial ventricular (AV) interval is greater than a selected constant value "x." If so, the flow proceeds along path 102 to operation 103, which determines if the subsequent VA interval is less than a selected constant value "y." In one embodiment, the values "x" and "y" could be, for example, 300 milliseconds and 150 milliseconds, respectively.

If the conditions of operation 103 are also satisfied, the flow proceeds along path 104 to operation 107, where the controller 24 initiates procedures to cause an atrial pace AP to be inserted after the preceding atrial paced or sensed event Ax at "z" milliseconds following the event Ax, where "z" is a programmable or selectable time interval following the event Ax. In one embodiment, an illustrative interval for "z" may be 100 milliseconds.

In one or more embodiments, rather than testing AV and VA as performed in operations 102 and 103, the method and apparatus may determine the ratio of the AV to VV interval in the absence of ventricular paced events, where "VV" is the interval between ventricular activations, for example, the interval between $VS_1$ and $VS_2$ in FIG. 3. For example, if the ratio of AV:VV exceeds >0.5 (or some other selectable desired value), an additional atrial pace is provided after a certain programmable duration "z" has elapsed following the first paced or intrinsic atrial event in the cycle.

Following insertion of the pace AP, one or more operations 111, 115, 119, 123 may be performed to determine if the additional pace AP was safely tolerated by the patient. The first operation 111 detects whether an increased AV condition ("Wenkebach") has occurred. "Wenkebach" can be described as progressively lengthening AV conduction intervals (i.e. Apace-Vsense intervals). Although it is common to observe Wenkebach in unpaced rhythms, higher rate atrial pacing can often lead to Wenkebach conduction. Often, if the atrial pacing rate is relatively high, the conduction time to the LV (observable as the PR interval) will progressively lengthen on a beat-to-beat basis because the AV node has insufficient time to reset and thus takes longer to conduct with each successive atrial pace. Eventually a ventricular beat is skipped and two atrial paces are observed with no ventricular event between them. The Wenkebach conduction phenomenon may also manifest itself, for example, as 3 atrial paces within a single ventricular cycle.

The second operation 115 performed according to FIG. 4 to determine whether the additional pace AP was safely tolerated detects whether the additional pace AP induced premature atrial contraction (PACs). The third operation 119 detects whether atrial tachycardia ("AT") or atrial fibrillation ("AF") has occurred. Finally, the fourth operation 123 determines whether the additional pace conducted 1:1. As reflected on the flow diagram of FIG. 4, if any one of the four tests performed in operations 111, 115, 119, 123 is satisfied ("Y"), the procedure of FIG. 4 is stopped, and no additional APs will be applied.

Thus, methods and apparatus have been disclosed for detecting and responding correctly to long AV delays by providing an additional atrial contraction within the same ventricular cycle to maintain AV mechanical ventricular coupling. While the methods and apparatus have been described in terms of what are presently considered to be specific embodiments, the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A method comprising:
   determining whether a current atrial-ventricular (AV) delay is adequate for proper mechanical coupling of an atrium and a ventricle in a patient; and
   generating an additional atrial contraction within a same ventricular cycle in response to a determination that said current AV delay is inadequate; and
   wherein said step of determining whether the current AV delay is adequate comprises determining whether an AV delay exceeds a selected duration and whether a ventricular-atrial (VA) delay is less than a selected duration.

2. The method of claim 1, wherein the step of generating an additional atrial contraction comprises delivering an atrial pacing pulse to the patient's heart.

3. The method of claim 1, further comprising performing at least one test to determine whether the additional atrial contraction was safely tolerated by the patient.

4. The method of claim 3, wherein the at least one test performed comprises performing one or more of:
   a first test to detect whether an increased AV condition (Wenkebach) has occurred;
   a second test to detect whether the additional pace induced premature atrial complexes;
   a third test to detect whether an atrial-tachycardia or atrial fibrillation has occurred, or
   a fourth test to determine whether the additional pace conducted 1:1.

5. An apparatus comprising:
   an implantable medical device;
   a controller in said device configured to cause pacing pulses to be applied to a patient's heart; and
   the controller further configured to detect whether a current atrial-ventricular (AV) delay is adequate for proper mechanical coupling of an atrium and a ventricle of the patient's heart, and if said current AV delay is inadequate, to cause an additional atrial pacing pulse to be delivered to the patient's heart within the same ventricular cycle; and
   wherein said controller is configured to determine whether an AV delay exceeds a selected duration and whether a ventricular-atrial (VA) delay is less than a selected duration.

6. The apparatus of claim 5, wherein the controller is configured to perform at least one test to determine whether the additional atrial contraction was safely tolerated by the patient.

7. The apparatus of claim 6, wherein the controller is configured to perform at least one test by performing one or more of:
   a first test to detect whether an increased AV condition (Wenkebach) has occurred;
   a second test to detect whether the additional pace induced premature atrial complexes;
   a third test to detect whether an atrial-tachycardia or atrial fibrillation has occurred; or
   a fourth test to determine whether the additional pace conducted 1:1.

8. A system comprising:
   means for determining whether a current atrial-ventricular (AV) delay is adequate for proper mechanical coupling of an atrium and a ventricle in a patient; and
   means for generating an additional atrial contraction within a same ventricular cycle in response to a determination that said current AV delay is inadequate; and
   wherein said means for determining whether the current AV delay is adequate comprises determining whether an AV delay exceeds a selected duration and whether a ventricular-atrial (VA) delay is less than a selected duration.

9. The system of claim 8, further comprising means for performing one or more tests to determine whether the additional atrial contraction was safely tolerated by the patient.

10. The system of claim 9, wherein said means for performing one or more tests performs one or more of:
   a first test to detect whether an increased AV condition (Wenkebach) has occurred;
   a second test to detect whether the additional pace induced premature atrial complexes;
   a third test to detect whether an atrial-tachycardia or atrial fibrillation has occurred; or
   a fourth test to determine whether the additional pace conducted 1:1.

* * * * *